United States Patent [19]

Komiya

[11] 4,335,713
[45] Jun. 22, 1982

[54] OTOSCOPE

[75] Inventor: Osamu Komiya, Hachioji, Japan

[73] Assignee: Olympus Optical Co., Ltd., Tokyo, Japan

[21] Appl. No.: 120,768

[22] Filed: Feb. 12, 1980

[30] Foreign Application Priority Data

Feb. 20, 1979 [JP] Japan .................................. 54/18737

[51] Int. Cl.³ ............................................. A61B 1/06
[52] U.S. Cl. ........................................... 128/9; 128/6
[58] Field of Search ...................................... 128/4–22

[56] References Cited

U.S. PATENT DOCUMENTS

| | | | |
|---|---|---|---|
| 1,431,902 | 10/1922 | Wolf | 128/6 |
| 2,162,681 | 6/1939 | Ryan | 128/6 |
| 3,543,746 | 12/1970 | Hotchkiss | 128/9 |
| 3,638,643 | 2/1972 | Hotchkiss | 128/22 |
| 3,727,605 | 4/1973 | Klein | 128/11 |
| 3,818,902 | 6/1974 | Kinoshita | 128/6 |

FOREIGN PATENT DOCUMENTS

| | | | |
|---|---|---|---|
| 605025 | 9/1960 | Canada | 128/6 |
| 1261275 | 2/1968 | Fed. Rep. of Germany | 128/6 |

*Primary Examiner*—Robert W. Michell
*Assistant Examiner*—Nancy A. B. Swisher
*Attorney, Agent, or Firm*—Frishauf, Holtz, Goodman & Woodward

[57] ABSTRACT

An otoscope comprises a guide tube which is to be inserted into the external auditory meatus of a patient and a side-viewing microscope which is reciprocated through the guide tube. A light beam direction-diverting device is provided in the distal end section of the guide tube. Where the microscope is in a retracted position, the light beam direction-diverting device faces an illumination window and observation window in the lateral wall of the distal end section of the microscope to divert light beams emitted from the illumination window ahead of the microscope in its axial direction and light beams conducted to the guide tube along the microscope toward the observation window. The microscope protrudes from the proximal end of the guide tube. When, therefore, the proximal end of the microscope is pushed into the guide tube, the distal end of the microscope protrudes from the distal end of the guide tube. A microscope-actuating device is provided between the guide tube and microscope. This microscope-actuating device normally locks the microscope in a retracted position. When manually operated, the microscope-actuating device lets the microscope protrude from the distal end of the guide tube. Mounted on the distal end of the guide tube is a protective ring which contacts the outer periphery of the external auditory meatus. Therefore, the protective ring ensures the insertion of the microscope into the middle ear and the protection of the inner wall of the middle ear, and further prevents a small hole previously opened in the eardrum from being unnecessarily enlarged.

25 Claims, 14 Drawing Figures

TO LIGHT SOURCE

TO LIGHT SOURCE

TO LIGHT SOURCE

TO LIGHT SOURCE

OTOSCOPE

BACKGROUND OF THE INVENTION

This invention relates to a midget endoscope and more particularly to an otoscope which can be inserted into the middle ear and carry out the safe and reliable observation of the middle ear.

The otoscope which is put into the middle ear through a small hole previously formed in the eardrum is generally of the rigit type. Therefore, the conventional otoscope is of the side-viewing type. However, the otoscope of the side-viewing type can not observe an object lying ahead in the axial direction and consequently is conducted unguidedly to the eardrum through the external auditory meatus and then to the middle ear through the eardrum. Therefore, the prior art otoscope has the serious drawbacks that unless the otoscope is inserted into the middle ear extremely carefully, the distal end of the otoscope will undesirably broaden a small hole opened in the eardrum or damage the inner wall of the middle ear.

SUMMARY OF THE INVENTION

An object of this invention is to provide an otoscope which comprises a guide tube capable of being introduced into the external auditory meatus, and a side-viewing type tubular microscope reciprocatively inserted into the guide tube, and whose distal end portion is equipped with a light beam direction-diverting device which, when the microscope is retracted into the guide tube, diverts the direction of illumination light beams delivered from the microscope ahead of the microscope in its axial direction and also directs image light beams brought in along the microscope toward an observation optical system of the microscope, thereby ensuring the safe and reliable insertion of the microscope into the middle ear.

Another object of the invention is to provide an otoscope wherein the microscope is normally retracted in the guide tube to let an illumination window and an observation window in the lateral wall of the distal end section of the microscope face the light beam direction-diverting device, and the proximal end of the microscope is pushed to let the distal end of the microscope to protrude from the distal end of the guide tube, thereby facilitating the changeover of the type of the otoscope from the direct-viewing to the side-viewing type or vice versa.

An otoscope embodying this invention comprises a guide tube which is inserted into the external auditory meatus and a side-viewing type microscope which is reciprocatively conducted into the guide tube. Provided in the distal end section of the guide tube is a light beam direction-diverting device which, when the microscope is in a retracted position, faces an illumination window and observation window formed in the lateral wall of the distal end section of the microscope, diverts light beams emitted from the illumination window ahead of the microscope in its axial direction, and diverts incoming light beams conducted to the guide tube along the microscope toward the observation window.

The microscope normally protrudes from the proximal end of the guide tube. Where, therefore, the proximal end of the microscope is pushed into the guide tube, the distal end of the microscope protrudes from the distal end of the guide tube. Provided between the guide tube and microscope is a microscope-actuating device which normally locks the microscope in a retracted position, and when it is actuated, it enables the microscope to be manually projected from the distal end of the guide tube.

A protective ring whose periphery contacts the external auditory meatus is mounted on the distal end section of the guide tube. This protective ring ensures the insertion of the microscope into the middle ear, the protection of the inner wall of the middle ear and further prevents a small hole previously opened in the eardrum from being unnecessarily broadened.

BRIEF DESCRIPTION OF THE DRAWING

This invention can be fully understood from the following description with reference to the accompanying drawings, in which.

DETAILED DESCRIPTION OF THE PREFERRED EMBODIMENTS

Referring to FIGS. 1 to 6, an otoscope 20 comprises a guide tube 21 and an elongated otoscope microscope 22 reciprocable through the guide tube 21.

Figure 4:
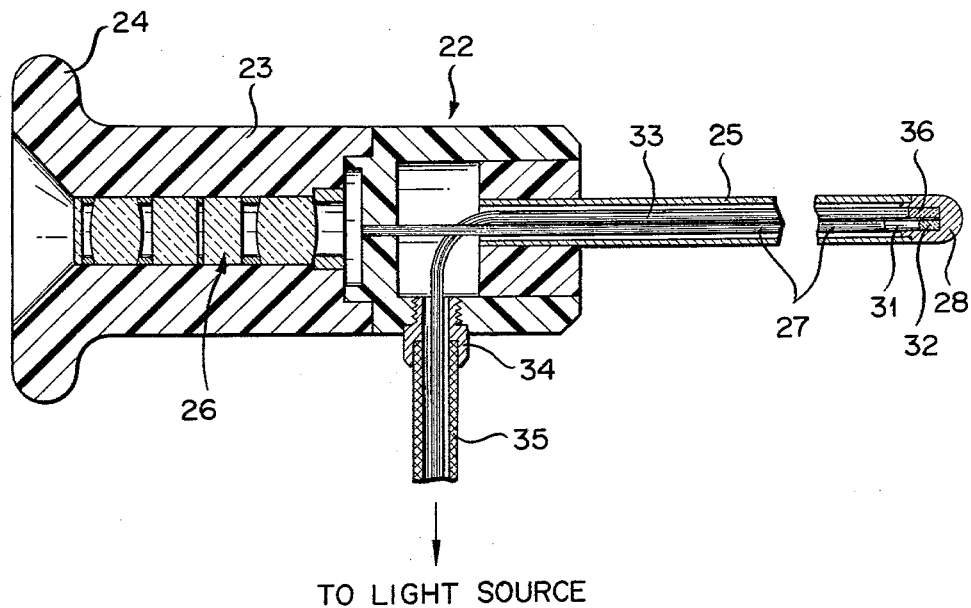
FIG. 4 is a longitudinal cross sectional view of the microscope of FIG. 1.

As best shown in FIG. 4, the microscope 22 is prepared from a hard material such as thermoplastic synthetic resin of, for example, polypropylene or polycarbonate, and comprises a cylindrical ocular section 23 having a flange 24 formed at its one end, and a narrow observation tube 25 which is formed of a rust-proof metal such as stainless steel or brass and axially protrudes from the distal end of the ocular section 23. Provided in the ocular section 23 is an eyepiece lens system 26 formed by combining an image-rotating prism with a plurality of concentrically arranged lenses. The observation tube 25 axially extends from the other end of the ocular section 23. One end of a relay lens 27 extending through the observation tube 25 protrudes from the proximal end of the observation tube 25 for optical connection to the ocular lens system 26.

Figure 5:
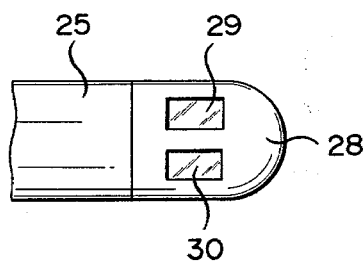
FIG. 5 is a top plan view of the distal end section of the microscope of FIG. 4.
Figure 6:
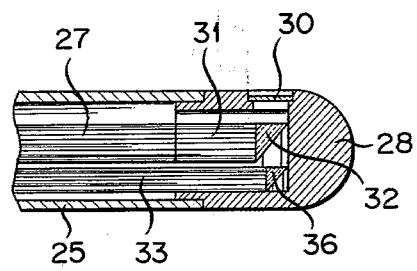
FIG. 6 is a longitudinal cross sectional view of FIG. 5.

The distal end section 28 of the observation tube 25 is blind. An illumination window 29 and observation window 30 are formed side by side in the circumferential direction of the blind distal end section 28 of the observation tube 25 (FIG. 5). Provided in the distal end section 28 of the observation tube 25 are an objective lens 31 such as a graded index lens (as set forth in the U.S. Pat. No. 3,801,181) which is aligned with the relay lens 27 and one end of which is optically connected to the other end of the relay lens 27, and a rectangular prism 32 which is set at the other end of the objective lens 31, and diverts light beams brought in from the observation window 30 at right angles. As a result, the light beams are conducted to the objective lens 31.

As seen from FIG. 4, an illumination optical fiber bundle 33 extending through the observation tube 25 along the relay lens 27 passes through a joint 34 projecting from the forward lateral wall of the ocular section 23, and also through a flexible tube 35 extending from the joint 34. One end of the illumination optical fiber bundle 33 is connected to a light source (not shown), and the other end of the optical fiber bundle 33 is optically connected to a rectangular prism 36 provided in the distal end section 28 of the observation tube 25 so as to face the illumination window 29. Light beams emitted from the light source and guided through the optical fiber bundle 33 are diverted by the rectangular prism 36 at right angles to be emitted from the illumination window 29 radially of the observation tube 25.

The guide tube 21 comprises a hollow cylindrical proximal end section 37 through which the ocular section 23 slides, and whose inner diameter has substantially the same measurement as the outer diameter of the ocular section 23; and a conical distal section 39 which is provided with a substantially conical hole 40 connected to a cylindrical hole 38 and a long cylindrical hole 41 which is contiguous to the conical hole 40 and has a sufficiently large inner diameter to allow for the passage of the observation tube 25.

The end face of the guide tube 21 is inclined at an angle of 45° to the axial line of the otoscope. A flange 42 is integrally formed with the distal end section 39 of the guide tube 21 in a state so inclined as to surround the inclined end face of the guide tube 21. The flange 42 is covered with a protective ring 43 prepared from a relatively pliable material such as rubber. This protective ring 43 has an annular groove 44 formed in the inner peripheral wall with a complementary shape to that of the inclined flange 42.

The protective ring 43 is chosen to have a sufficiently large outer diameter to touch the inner wall of the external auditory meatus. Protective rings 43 having different outer diameters are exchangeably provided to match the inner diameter of the external auditory meatus of a patient whose middle ear is to be examined.

Figure 1:
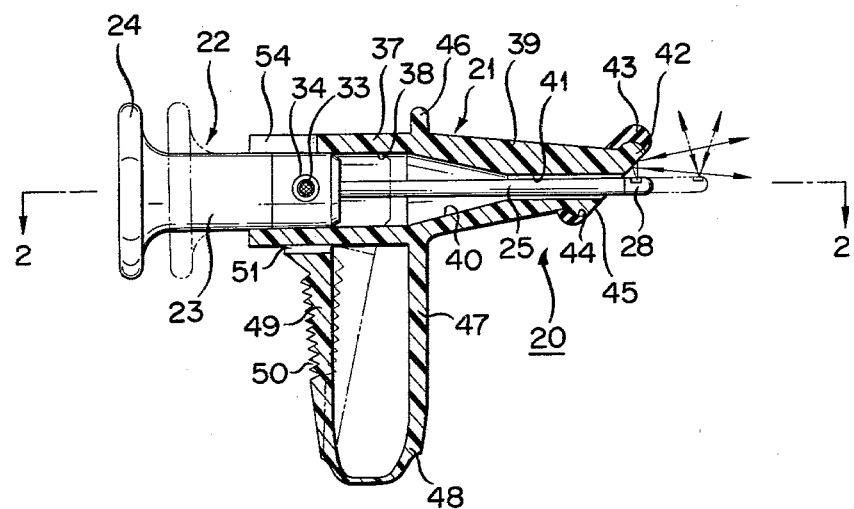
FIG. 1 is a longitudinal cross sectional view of an otoscope embodying this invention.
Figure 2:
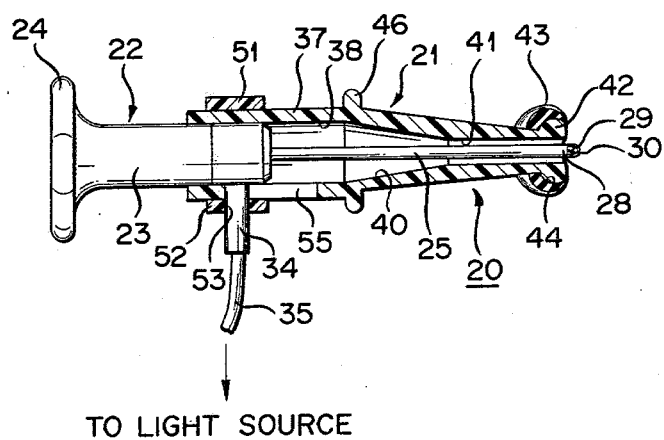
FIG. 2 is a cross sectional view on line 2—2 of FIG. 1.
Figure 3:
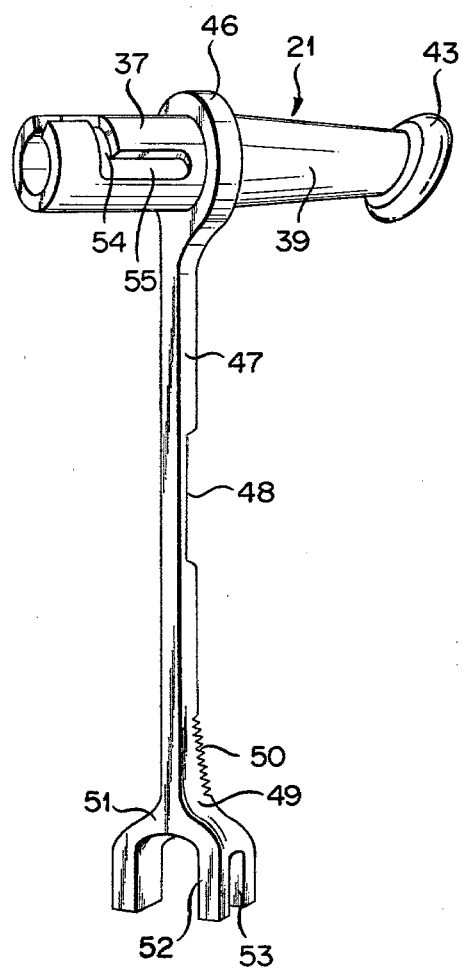
FIG. 3 is a perspective view of the guide tube of FIG. 1 with its operation handle unfolded.
Figure 7:
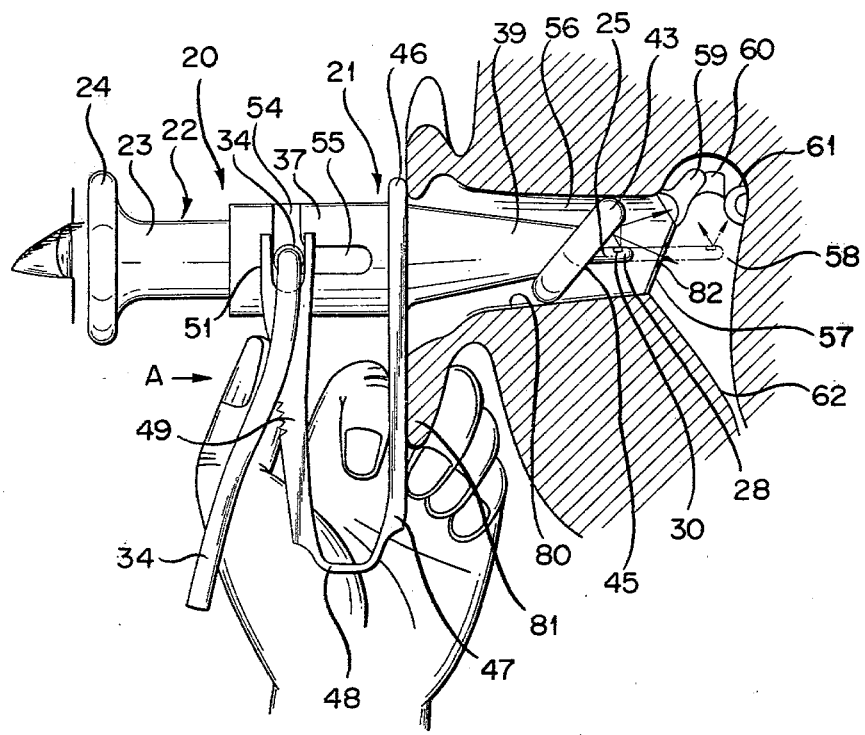
FIG. 7 shows an operation of the otoscope of FIG. 1.
Figure 8:
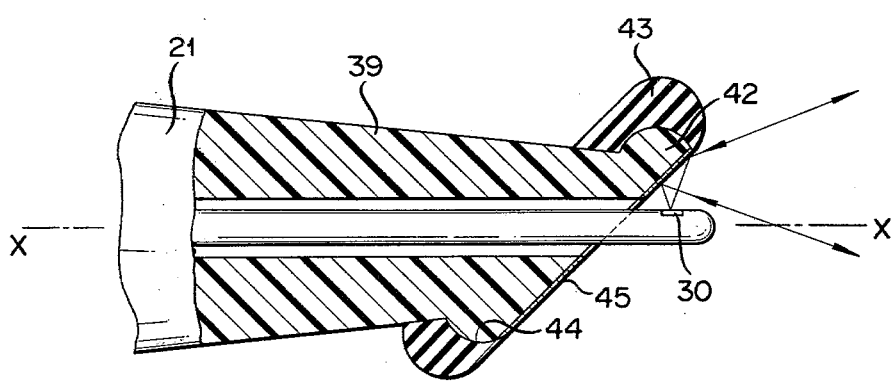
FIG. 8 is an enlarged longitudinal cross sectional view of the distal end section of the guide tube of FIG. 1.

The end face portion of the guide tube 21 is smoothly polished and plated with silver, thus constituting a silver reflection plane or mirror 45 inclined at an angle of 45° to the axis X—X of the guide tube 21 (FIG. 8). An annular flange or ear abutment 46 is integrally formed with the proximal end section 37 and distal end section 39 of the guide tube 21 at the boundary therebetween. A belt-shaped operation handle 47 (FIG. 3) which is formed of the same material as the guide tube radially extends outward from the flange-shaped ear abutment 46. An intermediate part 48 of the belt-shaped handle 47 is thin and easily bent so that the handle 47 forms a U-shape. The opposite rear-end portion of the handle 47 to the flange-shaped ear abutment 46 is thick to form a finger abutment 49 provided with a slip-stop knurled portion 50. The rear-end portion of the handle 47 forms a forked engagement section 51 whose inner wall has a semicircular cross section complementary to the outer peripheral surface of the proximal end section 37 of the guide tube 21 (FIG. 3 shows the extended free state of the handle 47). One prong 52 of the forked engagement section 51 is provided with an engagement groove 53 extending lengthwise of the handle 47. The joint 34 of the microscope 22 is fitted into the engagement groove 53 (FIGS. 2 and 7).

Formed in the peripheral wall of the proximal end section 37 of the guide tube 21 is a groove 54 which first axially extends from the free end of the proximal end section 37, then circumferentially extends along the peripheral surface thereof, and last again axially extends toward the distal end section 39 of the guide tube 21 (FIG. 3). Where the captioned otoscope is assembled by inserting the microscope 22 into the guide tube 21, the joint 34 of the ocular section 23 is put into the groove 54 from the proximal end section of the guide tube 21 and finally into a guide groove 55 (FIG. 7) constituting the terminal section of the groove 54. Therefore, the stroke of the inserted microscope 22 is defined by the length of the terminal groove 55. Where the joint 34 of the occular section 23 is set at that end of the terminal guide groove 55 which faces the proximal end section 37 of the guide tube 21, the illumination window 29 and observation window 30 formed in the peripheral wall of the distal end section 28 of the observation tube 25 lie in a region covered by the reflection plane or mirror 45. In other words, the illumination window 29 and observation window 30 face the reflection plane 45 of the guide tube 21. The other end of the terminal guide groove 55 is brought to that point on the proximal end section 37 of the guide tube 21 at which the distal end section 28 of the observation tube 25 can be fully projected into the middle ear.

Obviously, the measurements of an otoscope 20 vary with the age, sex, and race of a patient. With an otoscope adapted for use with the adult, however, the observation tube is chosen to have a length of 80 millimeters, an outer diameter of 1.7 millimeters and a stroke of 5 millimeters. The outer diameter of the proximal end section 37 of the guide tube 21 and the length of the distal end section 39 thereof are respectively chosen to have 12 millimeters and 40 millimeters. Further, the oblong protective ring 43 is defined to have a major axis of 11 to 13 millimeters and a minor axis of 8 to 10 millimeters. The middle ear has as small a depth as 3 to 4 millimeters even for the adult. Therefore, the illumination window 29 and observation window 30 are arranged side by side in the circumferential direction on the peripheral wall of the distal end section 28 of the observation tube 25, thereby preventing these windows 29, 30 from jointly occupying a space considerably extending toward the bottom of the middle ear.

The operation of the otoscope 20 according to one embodiment of this invention is described with reference to FIG. 7. The distal end section 39 of the guide tube 21 is inserted into the external auditory meatus 80 of a patient with the handle 47 left free. The operator puts the middle finder of his left hand on the inner wall of the lower part of a patient's ear 81 (that is, the earlobe). The operator places by the forefinger of the left hand that portion of the handle 47 which lies near the annular flange 46 on the outside of the earlobe of a patient. As a result, the annular flange 46 is brought to an entrance to the external auditory meatus 80 of the patient's ear 81. Since the protective ring 43 used has an outer diameter previously matched with the diameter of the external auditory meatus 80 of a patient, the peripheral wall of the protective ring 43 contacts the inner wall of the external auditory meatus 80. Therefore, the guide tube 21 is kept at rest relative to the external auditory meatus 80.

Light beams emitted from a light source conducted through the illumination optical fiber bundle 33 and reflected at right angles by the rectangular prism 36 are thrown forward from the illumination window 29 by means of the inclined reflection plane 45 of the distal end section of the guide tube 21 to illuminate the eardrum 57 of the patient. Light beams delivered from the eardrum 57 along the observation tube 25 is radially reflected by the reflection plane 45, conducted through the observation window 30, again reflected by the rectangular prism 32 and brought to the eyepiece lens system 26 through the objective lens 31 and relay lens 27, thereby producing an image of the eardrum 57. Under this condition, the otoscope 20 acts as the front-viewing type.

Except for the case where the eardrum 57 is originally broken, a small hole 82 is formed in advance by means of an ear microscope (or otomicroscope) and scalpel in a size sufficiently large to allow for the passage of the observation tube 25. The operator puts his eye to the proximal end of the ocular section 23 to look at the eardrum 57 and aligns the distal end section 28 of the observation tube 25 with the small hole 82 previously opened in the eardrum 57. The operator pushes the finger abutment 49 of the handle 47 by the thumb in the direction of an arrow A indicated in FIG. 7 against the elastic force of the handle 47 to let the observation tube 25 protrude from its place. As a result, the distal end section 28 of the observation tube 25 is inserted into the middle ear 58 through the small hole 82 previously opened in the eardrum 57 as shown in chain lines in FIG. 4. In this case, the distal end section 28 of the observation tube 25 lies outside of a region covered by the reflection plane 45, and does not receive light beams reflected from the reflection plane 45. Accordingly, the otoscope 20 acts as the side-viewing type, making it possible to observe the hammer 59, anvil 60 and stirrup 61 and inner wall 62 all of the middle ear 58.

When the operator's thumb is released from the finger abutment 49, the microscope 22 is retracted by the elastic force of the handle 47, causing the observation tube 25 to be pulled out of the middle ear 58 through the small hole 82 in the eardrum 57 previously opened therein. As a result, the microscope 22 regains its original position shown in solid lines in FIG. 7. Since the inner diameter of the external auditory meatus 80 varies with a patient, protective rings 43 having different sizes are exchangeably provided.

As previous described, the guide tube 21 can be easily and reliably set immovable relative to the external auditory meatus 80 of a patient, making it possible to insert the observation tube 25 exactly into the middle ear 58 through the small hole 82 opened in the eardrum 57. Since, further, the observation tube 25 is saved from crosswise shaking, the difficulties are little likely to arise that the small hole 82 opened in the eardrum 58 is unnecessarily broadened or the various organs enclosed in the middle ear 58 and the inner wall 62 of the middle ear 58 are damaged.

Figure 9:
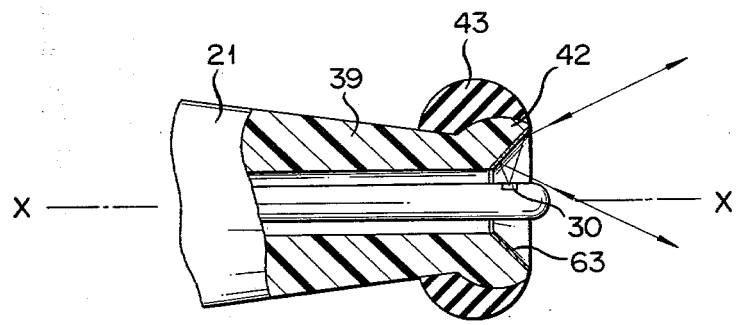
FIGS. 9 to 11 are other modifications of the distal end section of the guide tube embodying the invention.

With a light beam direction-diverting device according to an embodiment shown in FIGS. 1 to 8, the distal end section 39 of the tube 21 is fitted with an inclined reflection plane 45. With a light beam direction-diverting device according to an embodiment shown in FIG. 9, however, the distal end section of a guide tube 21 is formed into a truncated conical shape which is opened at the base and whose side wall is inclined at an angle of 45° to the axial line X—X of the guide tube 21. The inclined side wall is polished and plated with silver to constitute a reflection plane or conical reflection mirror 63 of the truncated conical form.

Figure 10:
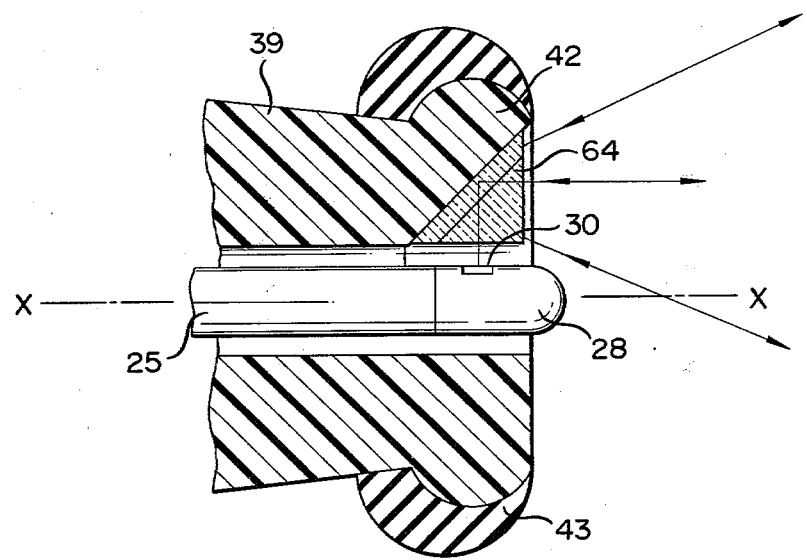

A light beam direction-diverting device according to an embodiment shown in FIG. 10 comprises a roof prism 64 provided in the distal end section 39 of a guide tube 21.

Figure 11:
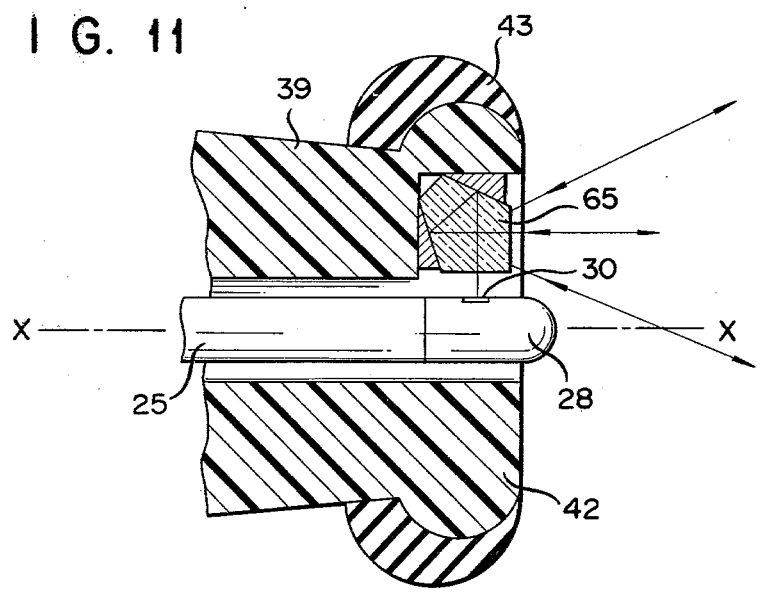

A light beam direction-diverting device according to an embodiment shown in FIG. 11 comprises a pentagonal prism 65 set in the distal end section 39 of a guide tube 21. Both types of light beam direction-diverting device are useful for the direct-viewing operation.

Figure 12:
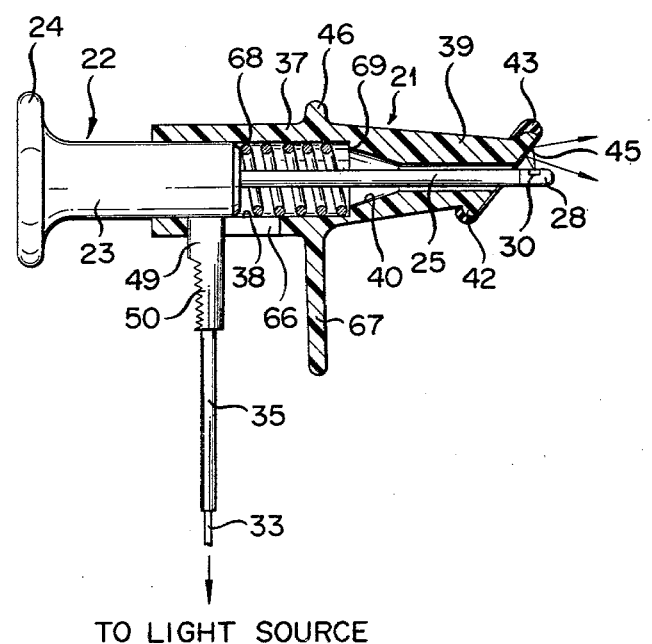
FIG. 12 shows an otoscope according to another embodiment of the invention.

With an otoscope according to an embodiment shown in FIG. 12, a finger abutment 49 provided with a slip-stop knurled section 50 is fixed to the ocular section 23 of the microscope 22. The finger abutment 49 protrudes outward through an axially extending guide groove 66 formed in the lateral wall of the proximal end section 37 of a guide tube 21. An illumination optical fiber bundle 33 extends through the finger abutment 49, and is further conducted through a flexible tube 35 to be conneted to a light source (not shown).

An earlobe abutment 67 projects from an annular flange 46 formed at the boundary between the proximal end section 37 and distal end section 39 of the guide tube 21 and is arranged parallel with the finger abutment 49 on the same side as the finger abutment 49.

A compression helical coil spring 68 is provided in a cylindrical hole 38 extending through the proximal end section 37 up to the distal end section 39 thereof. One end of this helical coil spring 68 is engaged with a shoulder section 69 defined between the cylindrical hole 38 and a truncated conical hole 40 formed in the distal end section 39 of the guide tube 21. The other end of the helical compression coil spring 68 is engaged with the distal end of the ocular section 23. The helical compression coil spring 68 normally elastically urges the microscope 22 toward the proximal end of the guide tube 21.

The guide groove 66 is chosen to have such length that when the microscope 22 is brought nearest to the proximal end of the guide tube 21, the illumination window 29 and observation window 30 opened in the peripheral wall of the distal end section 28 of the observation tube 25 face the inclined reflection plane 45 formed in the distal end section of the guide tube 21, and when the microscope 22 is drawn nearest to the distal end section of the guide tube 21, the distal end section 28 of the observation tube 25 can be fully inserted into the middle ear of a patient. The otoscope according to the embodiment of FIG. 12 is constructed in the same manner as that of FIGS. 1 to 8 in other respects than described above, and is operated in substantially the same manner.

Figure 13:
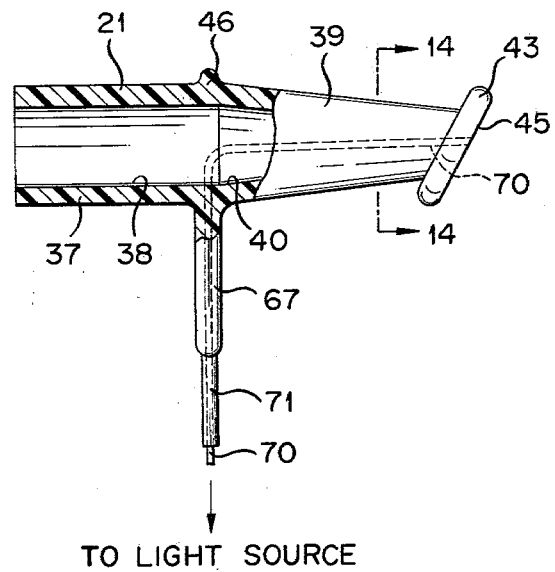
FIG. 13 indicates an otoscope according to a further embodiment of the invention.
Figure 14:
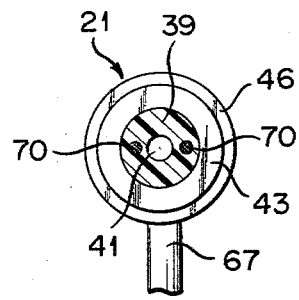
FIG. 14 is a cross sectional view on line 14—14 of FIG. 13.

With an otoscope according to an embodiment shown in FIGS. 13 and 14, a pair of illumination optical fiber bundles 70 are embedded in the lateral wall of the guide tube 21. One end of the illumination optical fiber bundles 70 extends through the distal end section 39 of the guide tube 21. The other end of the illumination optical fiber bundles 70 is connected to a light source (not shown) through an earlobe abutment 67 radially extending from the annular flange 46 and a flexible tube 71 connected to the earlobe abutment 67. The illumination optical fiber bundles allow for the illumination of the interior of the middle ear through the thin eardrum, enabling said interior to be very easily observed.

What is claimed is:

1. An otoscope which comprises:
   a guide tube which has a distal end section and a proximal end, and which is adapted to be inserted into an external auditory meatus;
   an elongated microscope which comprises a distal end section having a lateral wall and a proximal end section, and which is reciprocable through the guide tube in the axial direction of the guide tube between a first position at the proximal end of said guide tube whereat the microscope functions as a direct-viewing scope and a second position in said guide tube whereat the microscope functions as a side-viewing scope, the elongated microscope including an observation window and an illumination window disposed in the lateral wall of the distal end section of the microscope;
   an observation optical system and an illumination optical system which respectively face and which are respectively optically connected to the observation window and illumination window of the microscope when the microscope is in said first position, and which axially extend through the microscope, said observation and illumination optical systems being out of optical communication with both of said observation and illumination windows when the microscope is in said second position;
   a light beam direction-diverting means provided in the distal end section of the guide tube, and, when made to face the observation window and illumination window, diverts light beams delivered from the illumination optical system axially of the microscope, and diverts light beams coming in the axial direction of the microscope to the observation window; and
   a microscope-actuating means provided between the guide tube and the microscope, for reciprocating the microscope relative to the guide tube, and including means for normally elastically urging the microscope from its second position to its first position at the proximal end of the guide tube.

2. The otoscope according to claim 1, wherein said light beam direction-diverting means comprises a reflection surface convergently inclined to the guide tube.

3. The otoscope according to claim 2, wherein said reflection surface is a plane mirror.

4. The otoscope according to claim 2, wherein the reflection surface takes a truncated conical form.

5. The otoscope according to claim 2, wherein said reflection surface is a silver plated surface.

6. The otoscope according to claim 1, wherein said light beam direction-diverting means comprises a prism.

7. The otoscope according to claim 6, wherein said prism is a roof prism.

8. The otoscope according to claim 6, wherein said prism is a pentagonal prism.

9. The otoscope according to claim 1, wherein said microscope-actuating means comprises a U-shaped handle which is made of elastic material and has two ends, one of which is connected to the guide tube, and the other of which is connected to the microscope.

10. The otoscope according to claim 9, wherein said handle comprises a belt-shaped member having a thin elastically flexible intermediate section.

11. The otoscope according to claim 1, wherein said microscope comprises a projecting member extending from said lateral wall of the microscope; and the guide tube comprises a lateral wall, and an axially extending guide groove formed in the lateral wall of the guide tube and through which the projecting member of the microscope passes, for defining a stroke of the microscope reciprocating through the guide tube.

12. The otoscope according to claim 11, wherein said projecting member comprises a joint for causing the illumination optical system to be drawn out of the microscope.

13. The otoscope according to claim 12, wherein said microscope-actuating means comprises a U-shaped handle which is made of elastic material, and has two ends, one end being fixed to the lateral wall of the guide tube, and the other end being engaged with the joint of the microscope.

14. The otoscope according to claim 12, wherein said microscope-actuating means comprises the projecting member and a helical compression coil spring provided in the guide tube to urge the microscope to the proximal end of the guide tube.

15. The otoscope according to claim 14, wherein said projecting member comprises a finger abutment.

16. The otoscope according to claim 15, wherein said illumination optical system passes through the finger abutment.

17. The otoscope according to claim 1, further comprising a protective ring made of elastic material mounted on the distal end of the guide tube.

18. The otoscope according to claim 17, comprising an annular flange formed at the distal end of the guide tube; and wherein the protective ring comprises an inner annular groove engageable with the annular flange.

19. The otoscope according to claim 17, wherein the protective ring is replaceable.

20. The otoscope according to claim 17, wherein said guide tube comprises a lateral wall, and an ear abutment and earlobe abutment mounted on said lateral wall.

21. The otoscope according to claim 1, wherein said guide tube comprises at least one optical fiber bundle which axially extends through the guide tube from the distal end of the guide tube to be connected to a light source set outside of the guide tube.

22. An otoscope which comprises:
   a guide tube which has a distal end section and a proximal end, and which is adapted to be inserted into an external auditory meatus;
   an elongated microscope which comprises a distal end section having a lateral wall and a proximal end section, and which is reciprocable through the guide tube, the elongated microscope including an observation window and an illumination window disposed in the lateral wall of the distal end section of the microscope;
   an observation optical system and an illumination optical system which are respectively optically connected to the observation window and illumination window of the microscope, and which axially extend through the microscope;
   a light beam direction-diverting means provided in the distal end section of the guide tube, and, when made to face the observation window and illumination window, diverts light beams delivered from the illumination optical system axially of the microscope, and diverts light beams coming in the axial direction of the microscope to the observation window;

a microscope-actuating means provided between the guide tube and the microscope, for reciprocating the microscope relative to the guide tube, and including means for normally elastically urging the microscope to the proximal end of the guide tube; and a protective ring made of elastic material mounted on the distal end of the guide tube.

23. The otoscope according to claim 22, comprising an annular flange formed at the distal end of the guide tube; and wherein the protective ring comprises an inner annular groove engageable with the annular flange.

24. The otoscope according to claim 22, wherein the protective ring is replaceable.

25. The otoscope according to claim 22, wherein said guide tube comprises a lateral wall, and an ear abutment and earlobe abutment mounted on said lateral wall.

* * * * *